United States Patent [19]

O'Lenick, Jr.

[11] Patent Number: 5,068,324

[45] Date of Patent: Nov. 26, 1991

[54] NOVEL AMPHOTERIC POLYMERS

[75] Inventor: Anthony J. O'Lenick, Jr., Lilburn, Ga.

[73] Assignee: LCE Partnership, Lake Geneva, Wis.

[21] Appl. No.: 402,649

[22] Filed: Sep. 5, 1989

[51] Int. Cl.$^5$ .................. C07D 521/00; A61K 7/50
[52] U.S. Cl. .................. 540/471; 540/473; 540/474; 424/70; 424/71; 252/542
[58] Field of Search .................. 540/471, 473, 474

[56] References Cited

U.S. PATENT DOCUMENTS 3,860,576  1/1975  Ham et al. .................. 540/474

Primary Examiner—Robert T. Bond

[57] ABSTRACT

The present invention deals with novel amphoteric polymers and their application as softening, anti-tangle, and conditioning agents. The properties of these novel compositions which make them well suited for these applications is their substantivity to fibers, hair and skin and that they are very mild to the skin and eyes. The subject compositions are prepared by the polymerization of amphoteric monomers compounds with epichlorohydrin. The amphoteric monomer compounds are prepared by the reaction of commercially available multifunctional amines with an alpha beta unsaturated acid.

10 Claims, No Drawings

NOVEL AMPHOTERIC POLYMERS

BACKGROUND OF THE INVENTION

1. Field of the Invention

The present invention deals with the composition, and application of novel amphoteric polymers useful as softening, anti-tangle, and conditioning agents for use in personal care, textile and related applications. The properties of these novel amphoteric polymeric compositions which makes them well suited for these applications is the fact that they are substantive to fibers, hair and skin and also very mild to the skin and eyes.

2. Description of the Art Practices

Aminocarboxylic amphoteric surfactants have been known and used commercially for many years. Perhaps the most important early patent on the production of these materials is U.S. Pat. No. 2,195,974 to Reppe et al. The patent, issued in May 1936 and assigned to I. G. Farben, discloses the reaction of acrylic acid, methacrylic acid and ammonia or organic amines at temperatures at which amides do not form. The patent described many reaction conditions in addition many solvents were described ranging from water to other protic solvents. Reppe also described many so called "acrylic sources", which are suitable as raw materials for preparation of this class of amphoteric surfactants.

The surfactant properties of aminocarboxylic acids and salts are likewise well known to those skilled in the art. Over the years, these compounds have been found to be useful in as foaming agents and detergents in shampoos, cosmetics and detergents. The compounds have not enjoyed wider use in other applications, due to the fact that using the standard commercially available fatty amines (e.g. primary lauryl amine) the obtainable surfactant and physical properties are limited by the available hydrophobes. A product which lacks surfactant properties is obtained if the hydrophobe was too low in molecular weight (i.e. below 6 carbon). In many applications a higher molecular weight product would have some of the desired properties, like foam or wetting, but lack the desired water solubility.

Conversely, the selection of amines that are highly hydrophobic (C14 and above) results in other applications/performance problems. In the instance were high molecular weight amines are used solid products with poor water dispersibility result. The lack of solubility of these higher molecular weight products in aqueous systems, severely limits their potential in many applications. It has long been a desire of many industries to obtain an amphoteric surfactant having greater oil solubility and a liquid form. Until the compositions of this invention such a product was not obtainable.

U.S. Pat. No. 3,417,136 issued to Hovden Dec. 17, 1968, overcomes the former problem described, namely increased water solubility by incorporating in ether function into the molecule. Hovden states prior to his invention, the known aminocarboxylic acid surfactant compounds have a lesser water solubility than is desired in some applications. Further, he states many of these compounds do not have as great a wetting power as might be desired for certain applications. This is also a function of water solubility. While Hovden's invention solved the difficulty of obtaining a series of products which are more water soluble and have improved wetting properties, it remained a problem to produce higher molecular weight products having greater oil solubility and the desired properties of liquidity, lubrication, and emollient properties.

Quaternaries have been the compounds most commonly used to obtain the desired conditioning and softening properties. Amphoteric compounds have not enjoyed significant utility in this area. Standard quaternary compounds are prepared by quaternization of a tertiary amine with such agents as benzyl chloride or di-methyl sulfate of di-ethyl sulfate or methyl chloride. These materials are relatively inexpensive but offer several key disadvantages. These include yellowing or fabrics, a tendency to build-up upon repeated treatment, and variability in hand (i.e. softness and feel). Standard softeners used are selected from the following classes:

Class #1: Alkyl Imidazoline Quaternary Compounds made from the quaternization of an imidazoline made by reacting diethylenetriamine, and a high molecular weight fatty acid such as stearic acid. The standard quaternizating agents are di-ethyl sulfate, or methyl chloride, or di-methyl sulfate, or methyl chloride or benzyl chloride.

Class #2: Alkyl or dialkyl tertiary amines quaternized with benzyl chloride or di-ethyl sulfate or methyl chloride or di-methyl sulfate Class #3: Quaternary compounds of ethoxylated, propoxylated or nonalkoxylated amido amines derived from the reaction of a high molecular weight fatty acid like stearic acid and a polyamine like diethylene triamine. The standard quaternizating agents are di-ethylsulfate or di-methyl sulfate or methyl chloride or benzyl chloride.

Class #4: Amido amine salts derived from partially acid neutralized amines.

It is known that under certain catalytic conditions, epichlorohydrin reacts with certain alcohols to give an intermediate which can be used to react with tertiary amines to quaternary compounds. U.S. Pat. No. 3,445,440 to Susi (May 1969, and U.S. Pat. No. 3,517,045 to Susi (June 1970) teaches the use of chlorohydroxypropyl ether to alkylate specific tertiary amines which are the reaction product of a primary fatty amine and ethylene or propylene oxide to give compounds conforming to the following structure:

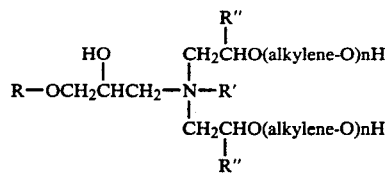

The Susi compounds are used as antistatic agents in polymeric compositions such as polyolefin. The antistatic properties of these compounds are achieved by the minimization of static charges on the polymer surface. These antistatic materials are incorporated into the polymer melt and are effective by virtue of their insolubility in the molten polymer. The quaternary compounds migrate to the polymer surface and are effective antistatic agents.

U.S. Pat. No. 4,144,122 to Emanuelsson issued Mar. 13, 1979 teaches that tallow alcohol and certain other higher molecular weight alcohols and their alkoxylates can be reacted with epichlorohydrin, then subsequently with tertiary amines to give compounds suitable for paper debonding.

U.S. Pat. No. 4,215,064 to Lindemann et al. issued July 29, 1980 teaches that phosphobetaines can be prepared by the reaction of a phosphate or phosphite salt with epichlorohydrin under aqueous conditions. U.S. Pat. No. 4,283,541 to O'Lanick, et al., issued Aug. 11, 1981 teaches the process for the preparation of the phosphobetaines described in Lindemann (U.S. Pat. No. 4,215,064). None of these patents teach the compounds of the present invention.

U.S. Pat. No. 4,800,077 issued January 1989 to O'-Lenick teaches that guerbet alcohols can be reacted with epichlorohydrin to give a chlorohydrin intermediate, which when reacted with an amine gives a quat compound.

There has been a long felt need in the industry for nonirritating polymeric materials which are substantive to hair skin and fiber. None of the prior art materials satisfactorily addressed these needs.

OBJECTS OF THE INVENTION

It is the object of this invention to produce high molecular weight amphoteric polymer compositions that have improved are highly substantive to hair, skin and fibers. This improved performance relates to the fact that the products of this invention are polymeric and high molecular weight which makes them less likely to cause irritation.

Another object of the invention is to provide a class of amphoteric compounds which are precursors for the polymerization.

Still another object of the invention is a process for the treatment of skin, hair and fibers with an effective conditioning amount of the polymeric compositions of the invention.

Other objects of the invention will become clear from the disclosure.

THE INVENTION

The first set of compounds of the present invention are the monomeric amphoteric units upon which the polymers are based. They are derived from amines which contain more than one amine group. These monomeric amphoteric compounds conform to the following structure:

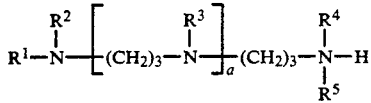

wherein:
  $R^1$ is alkyl having from 6 to 40 carbon atoms and in a preferred embodiment is selected from;

$CH_3-(CH_2)_n-$; $CH_3-(CH_2)_n-O-(CH_2)_3-$;

$CH_3-(CH_2)_m-O-(CH_2CH_2-O)_x-(CH_2CH(CH_3)O)_y-(CH_2CH_2-O)_z(CH_2)_3-$ $CH_3-(CH_2)_o-CHCH_2O-(CH_2CH_2O)_x-(CH_2CH(CH_3)O)_y-(CH_2CH_2O)_z(CH_{2o})_3-$;
   |
   $(CH_2)_pCH_3$ x, y, and z are independently integers from 0 to 20:
m, n, o, p are independently integers from 4 to 40:
a is an integer from 0 to 10.
$R^2$, $R^3$ and $R^4$ and $R^5$ are independently selected from $-CH_2CH_2COOM$, $-CH(CH_3)-CH_2COOM$ and $-CH_2C(CH_3)HCOOM$:

M is a cation needed for charge balance and is selected from Na, K, NH4, Li, and Ca.

The reaction of a primary amine or primary amine alkoxylates with varying amounts of acrylonitrile followed by hydrogenation to produce an amino amine or alkoxy aminoamine is well known to those skilled in the art and are commercially practiced by Tomah Products, Milton, Wis. The overall reaction is shown below:

$$RNH_2 + s\ CH_2CHC\equiv N \xrightarrow[\text{catalyst}]{H_2} R-NH[(CH_2)_3NH]_s-H$$

This invention is based upon the reaction of the above amino amine with an unsaturated carboxylic acid or ester selected from acrylic acid, methyl acrylate, crotic acid or methacrylic acid to produce a high purity tertiary amine compounds which are the monomers used in the preparation of the compounds of this invention.

The presence of more than one tertiary amine in the molecule allows for the subsequent polymerization by reaction with epichlorohydrin. This gives the desired crosslinked amphoteric polymer in high purity.

The second set of compositions of the present invention are polymeric amphoteric compositions prepared by the reaction product of the monomeric amphoterics shown above and epichlorohydrin. These compositions are mixtures which conform to the following formula;

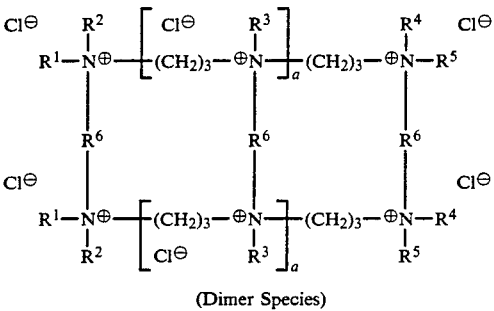

(Dimer Species)

and

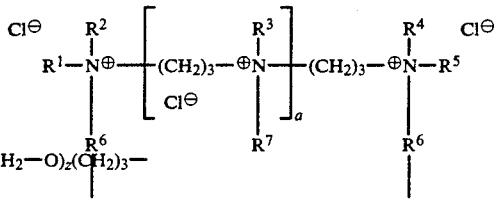

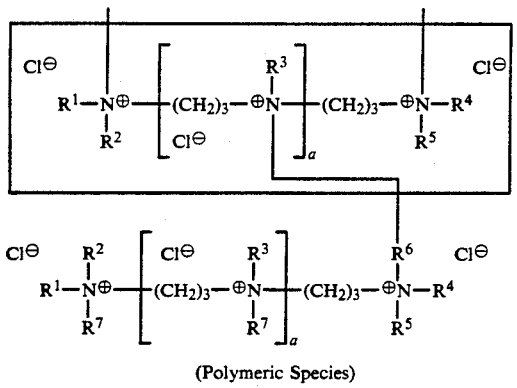

wherein:
$R^6$ is $-CH_2CH(OH)CH_2-$;
$R^7$ selected from H and $CH_2CH(OH)CH_2OH$
b is an integer from 0 to 100.

PREFERRED EMBODIMENT

In a preferred embodiment the amine used in the preparation of the diamine is based upon an alcohol. Such ether diamines conform to the following structure and are items of commerce from Tomah Products, Milton, Wis.

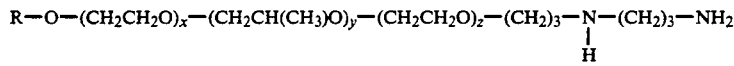

In another preferred embodiment x, y or z are greater than 0, the product is derived from an alkoxylated ether diamine. Ether diamine compounds of this type are commercially available from Tomah Products Milton, Wis. The synthesis of the monomeric materials will become more apparent later.

In still another preferred embodiment the alcohol used to make the ether polyamine is a Guerbet Alcohols, which are highly regiospecifically beta branched alcohols, that have been known since the 1890's when Marcel Guerbet first synthesized them. (M. Guerbet, C.R. Acad. Sci. Paris, 128. 511; 1002 (1899)). These materials are high in molecular weight and are liquid to very low temperatures. Unlike the oxo process and most other processes which result in low molecular weight (e.g. methyl and ethyl groups) random branches on the reactant alcohol, the guerbet reaction gives very specific branching in the alcohol at very high yields. The reaction sequence is the reason for this and is shown as follows:

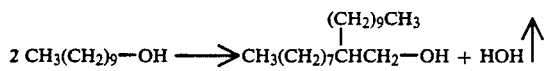

As can be seen by the above reaction the molecules have substitution on the second carbon from the hydroxyl group. This branching has been found to be critical to the preparation of a product having the desired properties. If the branching were on the same carbon as the hydroxyl group, the hydroxyl group would be a secondary one and would be very hindered and have low reactivity. As one moves the branch position away from the beta carbon, the liquidity, and substantivity to hair and fiber decreases.

The use of guerbet derived ether amines to prepare compositions of this invention results in substantive liquid products. The high molecular weight of the hydrophobe allows for better oil solubility using these surfactants over conventional nonionic surfactants.

As stated, another novel aspect of this invention is the use of alkoxylated ether diamines to make the amphoteric monomers useful as raw materials in the practice or a preferred embodiment of this invention. This results in polymeric amphoterics which exhibit an inverse cloud point in aqueous solution. The inverse cloud point phenomena which occurs as one heats an aqueous solution to a critical temperature has been well documented. More detailed descriptions of this are found in standard textbooks, such as A. M. Schwartz and J. W. Perry "Surface Active Agents", Vol. I (1949); and "Surface Active Agents and Detergents" Vol. II (1958). Interscience Publishers, New York, the descriptions of which are incorporated herein by reference. Standard amphoterics do not exhibit this cloud point phenomena. The product exhibiting this property is least soluble in water above the high cloud point, and has the maximum substantivity to metal and fiber. This property together with the liquidity and high molecular weight from the choice of the guerbet ether amine or guerbet ether amine alkoxylate, allows for the formulation of water based high efficiency lubricants for metal, hair and textile applications which can be easily formulated. Additionally, the products of this invention are ideally suited to extreme pressure lubricants where aqueous solutions heat up as a result of two metal parts generating friction. The water solution will heat to above the inverse cloud point, the amphoteric will become less soluble in water and form a film on the metal. Thus the lubricant is delivered to the surface of the metal were it is most needed.

The guerbet ether diamines and alkoxylated ether diamines, useful as raw materials for this invention are available commercially from Tomah Products, Milton, Wis. The use of guerbet alcohols results in outstanding and unique properties which will become more apparent.

The novel amphoteric surfactant compositions of the present invention include both acids and salts thereof, and in the above formula "M" may be hydrogen or any positively charged salt forming radical, e.g., alkali metal, ammonium or ethanolamine.

A key feature of the invention is the fact that the molecular weight of the polymeric compositions, and consequently performance of the compositions are controlled by process parameters including the pH at which the polymerization is run, the exact mole ratios of reactants used and the amount and type of solvent used. Of these the most important is pH. The pH of the aqueous solution in which polymerization is conducted has a profound on the molecular weight.

EXAMPLES

Commercially Available Amines

Commercially available amines useful for the preparation of the compounds of this invention conform to the following structure;

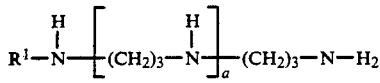

| | Class 1 $R^1$ is $CH_3-(CH_2)_n-$ | |
|---|---|---|
| Reactant Number | a | n |
| A | 0 | 17 |
| B | 0 | 15 |
| C | 0 | 13 |
| D | 1 | 11 |
| E | 1 | 9 |

| | Class 1 $R^1$ is $CH_3-(CH_2)_n-O-(CH_2)_3-$; | |
|---|---|---|
| Reactant Number | a | n |
| F | 0 | 11 |
| G | 0 | 9 |
| H | 1 | 13 |
| I | 2 | 15 |
| J | 0 | 17 |

| | Class 3 $R^1$ is $CH_3-(CH_2)_m-O-(CH_2CH_2O)_x-(CH_2CH(CH_3)O)_y-(CH_2CH_2O)_z(CH_2)_3-$; | | | | |
|---|---|---|---|---|---|
| Reactant Number | a | m | x | y | z |
| K | 0 | 17 | 0 | 0 | 0 |
| L | 0 | 15 | 1 | 0 | 5 |
| M | 1 | 13 | 10 | 10 | 10 |
| N | 4 | 11 | 0 | 10 | 5 |
| O | 0 | 9 | 20 | 20 | 20 |

Class 4
$R^1$ is
$CH_3-(CH_2)_o-CHCH_2O-(CH_2CH_2O)_x-(CH_2CH(CH_3)O)_y-(CH_2CH_2O)_z(CH_2)_3-$
                |
          $(CH_2)_pCH_3$

| Reactant Number | a | o | x | y | z | p |
|---|---|---|---|---|---|---|
| P | 4 | 7 | 9 | 0 | 0 | 0 |
| Q | 0 | 7 | 9 | 0 | 1 | 0 |
| R | 0 | 9 | 9 | 5 | 5 | 5 |
| S | 1 | 9 | 11 | 10 | 0 | 10 |
| T | 0 | 11 | 11 | 0 | 0 | 0 |

GENERAL PROCEDURE

In a suitable three neck flask equipped with agitation and thermometer, is added 1000 grams of water, 72.0 grams of acrylic acid and 500 ppm hydroquinone mono methylether. Next, the specified amount of the specified amine reactant (examples A-T) is added. The reaction mass will thicken as heat is applied. At about 80°-90° C. The viscosity thins out. Hold at this temperature 5 to 9 hours. The reaction is complete when the tertiary amine concentration reaches at least 97% of theoretical.

Add enough base to neutralize the product to a pH of 7 to 8. Addition is exothermic and is controlled by submersion of the flask into a cooling bath.

Next, slowly add the specified number of grams of epichlorohydrin under good agitation. The reaction is somewhat exothermic. Keep the temperature during the add below 70° C., since epichlorohydrine and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

EXAMPLES

| | Class 1 $R^1$ is $CH_3-(CH_2)_n-$ | | |
|---|---|---|---|
| Example Number | $R^2$ | $R^4$ | $R^5$ |
| 1 | CH2CH2COONa | CH2CH2COONa | CH2CH2COONa |

In a suitable three neck flask equipped with agitation and thermometer, is added 1,000 grams of water, 216.0 grams of acrylic acid and 500 ppm hydroquinone mono methylether. Next, add 287.0 of the amine reactant example 1. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add the enough NaOH to neutralize the product to a pH of 7 to 8. Addition is exothermic and is controlled by submersion of the flask into a cooling bath. The intermediate is an aqueous solution of the monomeric amphoteric.

Next, slowly add 93.0 grams of epichlorohydrin under good agitation. The reaction is somewhat exothermic. Keep the temperature during the add below 70° C., since epichlorohydrine and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

| Example Number | $R^2$ | $R^3$ | $R^4$ | $R^5$ |
| --- | --- | --- | --- | --- |
| 4 | CH2CH2COONa | CH2CH2COONa | CH2CH2COONa | CH2CH2COONa |

| Example Number | $R^2$ | $R^4$ | $R^5$ |
| --- | --- | --- | --- |
| 2 | CH2CH2COOK | CH2CH2COOK | CH2CH2COOK |

In a suitable three-neck flask equipped with agitation and thermometer, is added 1,000 grams of water, 216.0 grams of acrylic acid and 500 ppm hydroquinone mono methylether. Next, add 259.0 grams amine reactant example 2. The reaction mass will thicken as heat is applied at about 80°-90° C. the viscosity thins out. Hold at this temperature 5 to 9 hours. The reaction is complete when the tertiary amine concentration reaches at least 97% of theoretical.

Add enough KOH to neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrine and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

| Example Number | $R^2$ | $R^4$ | $R^5$ |
| --- | --- | --- | --- |
| 3 | CH2CHCOONa<br>\|<br>CH3 | CH—CH2COONa<br>\|<br>CH3 | CH2CH2COONa |

In a suitable three neck flask equipped with agitation and thermometer, is added 1000 grams of water, 72.0 grams of acrylic acid, 85.0 grams of crotonic acid, 85.0 grams of methacrylic acid and 500 ppm hydroquinone mono methylether. Next, add 231.0 grams of amine reactant example C. The reaction mass will thicken as heat is applied. At about 80°-90° C. the viscosity thins out. Hold at this temperature 5 to 9 hours. The reaction is complete when the tertiary amine concentration reaches at least 971% of theoretical.

Add enough NaOH to neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrine and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

In a suitable three neck flask equipped with agitation and thermometer, is added 1000 grams of water, 288.0 grams of acrylic acid and 500 ppm hydroquinone mono methylether. Next, add 236.0 grams of amine reactant example D. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add enough NaOH to neutralize the product to a pH of 7 to 8. Addition is exothermic and is controlled by submersion of the flask into a cooling bath.

Next, slowly add 139.5 grams of epichlorohydrin under good agitation. The reaction is somewhat exothermic. Keep the temperature during the ad below 70° C., since epichlorohydrine and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

| Example Number | $R^2$ | $R^3$ | $R^4$ | $R^5$ |
| --- | --- | --- | --- | --- |
| 5 | CH2CH2COONa | CH2CH2COONa | CH2CH2COONa | CH2CH2COONa |

In a suitable three neck flask equipped with agitation and thermometer, is added 1000 grams of water, 288.0 grams of acrylic acid and 500 ppm hydroquinone mono methylether. Next, add 208.0 grams of amine reactant example E. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add enough NaOH to neutralize the product to a pH of 7 to 8. Addition is exothermic and is controlled by submersion of the flask into a cooling bath.

Next, slowly add 139.5 grams of epichlorohydrin under good agitation. The reaction is somewhat exothermic. Keep the temperature during the add below 70° C., since epichlorohydrine and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

Class 2
$R^1$ is $CH_3-(CH_2)_n-O-(CH_2)_3-$:

| Example Number | $R^2$ | $R^3$ | $R^4$ | $R^5$ |
|---|---|---|---|---|
| 8 | CH2CH2COONa | CH2CH2COONa | CH2CH2COONa | CH2CH2COONa |

| Example Number | $R^2$ | $R^4$ | $R^5$ |
|---|---|---|---|
| 6 | CH2CH2COONa | CH2CH2COONa | CH2CH2COONa |

In a suitable three neck flask equipped with agitation and thermometer, is added 1000 grams of water, 216.0 grams of acrylic acid and 500 ppm hydroquinone mono methylether. Next, add 261.0 grams of amine reactant example F. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add enough NaOH to neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrine and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

In a suitable three neck flask equipped with agitation and thermometer, is added 1000 grams of water, 288.0 grams of acrylic acid and 500 ppm hydroquinone mono methylether. Next, add 322.0 grams of amine reactant example H. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add enough NaOH to neutralize the product to a pH of 7 to 8. Addition is exothermic and is controlled by submersion of the flask into a cooling bath.

Next, slowly add 139.5 grams of epichlorohydrin under good agitation. The reaction is somewhat exothermic. Keep the temperature during the add below 70° C., since epichlorohydrine and water will azeotropically boil. Once the addition is complete, generally one to three hours, heat to 90° C. Hold 3 l to 8 hours. Reaction is followed by % inorganic chloride.

The product is now present in aqueous solution and can be used without purification or can be dried down in a roto-evaporator if desired.

| Example Number | $R^2$ | $R^3$ | $R^4$ | $R^5$ |
|---|---|---|---|---|
| 9 | CH2CH2COONa | CH2CH2COONa | CH2CH2COONa | CH2CH2COONa | cally boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

In a suitable three neck flask equipped with agitation and thermometer, is added 1000 grams of water, 360.0 grams of acrylic acid and 500 ppm hydroquinone mono methylether. Next, add 383.0 grams of amine reactant example I. The reaction mass will thicken as heat is applied. At about 80°-90° C. the viscosity thins out.

| Example Number | $R^2$ | $R^4$ | $R^5$ |
|---|---|---|---|
| 7 | CH2CH2COONa | CH—CH2COONa<br>\|<br>CH3 | CH2CHCOONa<br>\|<br>CH3 |

In a suitable three neck flask equipped with agitation and thermometer, is added 1000 grams of water, 72.0 grams of acrylic acid, 85.0 grams of crotonic acid 85.0 grams of methacrylic acid and 500 ppm hydroquinone mono methylether. Next, add 233.0 grams of amine reactant example G. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add enough NaOH to neutralize the product to a pH of 7 to 8. Addition is exothermic and is controlled by submersion of the flask into a cooling bath.

Next, slowly add 186.0 grams of epichlorohydrin under good agitation. The reaction is somewhat exothermic. Keep the temperature during the add below 70° C. since epichlorohydrine and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

| Example Number | $R^2$ | $R^4$ | $R^5$ |
|---|---|---|---|
| 10 | CH2CH2COONa | CH2CH2COONa | CH2CH2COONa |

In a suitable three neck flask equipped with agitation and thermometer, is added 1000 grams of water, 216.0 grams of acrylic acid and 500 ppm hydroquinone mono methylether. Next, add 345.0 grams of amine reactant example J. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add enough NaOH base to neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

Add the enough NaOH to neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

| Example Number | $R^2$ | $R^4$ | $R^5$ |
|---|---|---|---|
| 12 | CH2CH2COOK | CH2CH2COOK | CH2CH2COOK |

In a suitable three neck flask equipped with agitation and thermometer, is added 1000 grams of water, 216.0 grams of acrylic acid and 500 ppm hydroquinone mono methylether. Next, add 581.0 grams of amine reactant example L. The reaction mass will thicken as heat is applied. At about 80°-90° C. the viscosity thins out. Hold at this temperature 5 to 9 hours. The reaction is complete when the tertiary amine concentration reaches at least 971% of theoretical.

Add enough KOH to neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 to 8 hours. Reaction is followed by % inorganic chloride.

| Class 3 $R^1$ is |||||
| $CH_3-(CH_2)_m-O-(CH_2CH_2O)_x-(CH_2CH(CH_3)O)_y-(CH_2CH_2O)_z(CH_2)_3-$; ||||
|---|---|---|---|
| Example Number | $R^2$ | $R^4$ | $R^5$ |
| 11 | CH2CH2COONa | CH—CH2COONa<br>\|<br>CH3 | CH2CHCOONa<br>\|<br>CH3 |

In a suitable three neck flask equipped with agitation and thermometer, is added 1000 grams of water, 72.0 grams of acrylic acid, 85.0 grams of crotonic acid, 85.0

The product is now present in aqueous solution and can be used without purification or can be dried down in a roto-evaporator if desired.

| Example Number | $R^2$ | $R^3$ | $R^4$ | $R^5$ |
|---|---|---|---|---|
| 13 | CH2CH2COONa | CH—CH2COONa<br>\|<br>CH3 | CH2CH—COONa<br>\|<br>CH3 | CH2CH2COONa | grams of methacrylic acid and 500 ppm hydroquinone mono methylether. Next, add 345.0 grams of amine reactant example K is added. The reaction mass will thicken as heat is applied. At about 80°-90° C. the viscosity thins out. Hold at this temperature 5 to 9 hours. The reaction is complete when the tertiary amine concentration reaches at least 97% of theoretical.

In a suitable three neck flask equipped with agitation and thermometer, is added 1000 grams of water, 144.0 grams of acrylic acid, 85.0 grams of crotonic acid, 85.0 grams of methacrylic acid and 500 ppm hydroquinone mono methylether. Next, 1791.0 grams of amine reactant examples M. The reaction mass will thicken as heat is applied. At about 80°-90° C. the viscosity thins out.

Hold at this temperature 5 to 9 hours. The reaction is complete when the tertiary amine concentration reaches at least 971% of theoretical.

Add enough NaOH to neutralize the product to a pH of 7 to 8. Addition is exothermic and is controlled by submersion of the flask into a cooling bath.

Next, slowly add 139.5 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

complete when the tertiary amine concentration reaches at least 971% of theoretical.

Add enough NaOH to neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 1 to 8 hours. Reaction is followed by % inorganic chloride.

The product is now present in aqueous solution and can be used without purification of can be dried down in a roto-evaporator if desired.

Class 4
$R^1$ is $$CH_3-(CH_2)_o-\underset{|}{C}HCH_2O-(CH_2CH_2O)_x-(CH_2CH(CH_3)O)_y-(CH_2CH_2O)_z(CH_2)_3-$$
$$(CH_2)_pCH_3$$

| Example Number | $R^2, R^3, R^4, R^5$ |
|---|---|
| 16 | CH2CH2COONa |

In a suitable three neck flask equipped with agitation

| Example Number | $R^2$ | $R^3$ | $R^4$ | $R^5$ |
|---|---|---|---|---|
| 14 | CH2CH2COONa | CH2CH2COONa | CH2CH2COONa | CH2CH2COONa |

In a suitable three neck flask equipped with agitation and thermometer, is added 1000 grams of water, 504.0 grams of acrylic acid and 500 ppm hydroquinone mono methylether. Next, 1236.0 grams of amine reactant example N. The reaction mass will thicken as heat is applied. At about 80°-90° C. the viscosity thins out. Hold at this temperature 5 to 9 hours. The reaction is complete when the tertiary amine concentration reaches at least 971% of theoretical.

Add enough NaOH to neutralize the product to a pH of 7 to 8. Addition is exothermic and is controlled by submersion of the flask into a cooling bath.

Next, slowly add 279.0 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

| Example Number | $R^2$ | $R^4$ | $R^5$ |
|---|---|---|---|
| 15 | CH2CH2COONa | CH2CH2COONa | CH2CH2COONa |

In a suitable three neck flask equipped with agitation and thermometer, is added 5000 grams of water, 216.0 grams of acrylic acid and 500 ppm hydroquinone mono methylether. Next, 3,133.0 grams of amine reactant example O. The reaction mass will thicken as heat is applied. At about 80°-90° C. the viscosity thins out. Hold at this temperature 5 to 9 hours. The reaction is and thermometer, is added 100 grams of water, 504.0 grams of acrylic acid and 500 ppm hydroquinone mono methylether. Next, add 564.0 grams of amine reactant example P. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add enough NaOH to neutralize the product to a pH of 7 to 8. Addition is exothermic and is controlled by submersion of the flask into a cooling bath.

Next, slowly add 279.0 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

| Example Number | $R^2$ | $R^4$ | $R^5$ |
|---|---|---|---|
| 17 | CH2CH2COONa | CH2CH2COONa | CH2CH2COONa |

In a suitable three neck flask equipped with agitation and thermometer, is added 1000 grams of water, 216.0 grams of acrylic acid and 500 ppm hydroquinone mono methylether. Next, add 419.0 grams of amine reactant example Q. the reaction mass will thicken as heat is applied. At about 80°-90° C. the viscosity thins out.

Hold at this temperature 5 to 9 hours. The reaction is complete when the tertiary amine concentration reaches at least 971% of theoretical.

Add enough NaOH to neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

| Example Number | $R^2$ | $R^4$ | $R^5$ |
|---|---|---|---|
| 18 | CH2CH2COOLi | CH2CH—COOLi<br>\|<br>CH3 | CH—CH2COOLi<br>\|<br>CH3 |

In a suitable three neck flask equipped with agitation and thermometer, is added 1000 grams of water, 72.0 grams of acrylic acid, 85.0 grams of crotonic acid, 85.0 grams of methacrylic acid and 500 ppm hydroquinone mono methylether. Next, add 1139.0 grams of amine reactant example R. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add enough LiOH neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

| Example Number | $R^2 R^3 R^4$ and $R^5$ |
|---|---|
| 19 | CH2CH2COOK |

In a suitable three neck flask equipped with agitation and thermometer, is added 1000 grams of water, 288.0 grams of acrylic acid and 500 ppm hydroquinone mono methylether. Next, add 1743.0 grams of amine reactant example S. The reaction mass will thicken as heat is applied. At about 80°-90° C. the viscosity thins out. Hold at this temperature 5 to 9 hours. The reaction is complete when the tertiary amine concentration reaches at least 97% of theoretical.

Add enough KOH to neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

| Example Number | $R^2$ | $R^4$ | $R^5$ |
|---|---|---|---|
| 20 | CH2CH2COONa | CH2CH2COONa | CH2CH2COONa |

In a suitable three neck flask equipped with agitation and thermometer, is added 1000 grams of water, 216.0 grams of acrylic acid and 500 ppm hydroquinone mono methylether. Next, add 488.0 grams of amine reactant example T. The reaction mass will thicken as heat is applied. At about 80°-90° C. the viscosity thins out. Hold at this temperature 5 to 9 hours. The reaction is complete when the tertiary amine concentration reaches at lest 97% of theoretical.

Add enough NaOH neutralize the product to a pH of 7 to 8. Addition is exothermic and is controlled by submersion of the flask into a cooling bath.

Next, slowly add 93.0 grams of epichlorohydrin under good agitation. The reaction is somewhat exothermic. Keep the temperature during the add below 70° C., since epichlorohydrin and water will azeotropically boil. Once the addition is complete, generally one to three hours, heat to 90° C. Hold 3 to 8 hours. Reaction is followed by % inorganic chloride.

The product is now present in aqueous solution and can be used without purification or can be dried down in a roto-evaporator if desired.

APPLICATIONS EXAMPLES

The compositions of this invention can be formulated into softeners that are applied directly in aqueous solution by themselves or formulated with anionic, nonionic or amphoteric surfactants and builders to prepare finished conditioner/detergent systems. The level of composition of the present invention is typically used at a weight ratio to water of about 1:10:000 to 1:20 to soften fabric. Conditioners and Shampoos using the compositions employ it at 21% to 30% by weight. Anionic surfactants include lauryl and stearyl sulfate as well as alkylbenzene sulfonates, preferably the sodium salts. Nonionic surfactants include alkylalkoxylates typically having from 10 to 20 carbon atoms in the alkyl group and from 1 to 10 alkylene oxide units (preferably ethylene). Builders include the phosphates STPP and SPP as well as aluminosilicates.

COLOR FASTNESS APPLICATION DATA

Compositions of this invention were compared to standard compounds commercially available using AATCC Test Method 117-1979. The color fastness heat test uses a 400° F. (205° F.) hot iron which is applied for 60 and 180 seconds. The color is rated on a 1–5 basis for yellowness, (5 being the most yellow).

| Compound | CAS Number | Yellowness |
|---|---|---|
| Alkaquat O | 68122-86-1 | 4 |

| Compound | CAS Number | Yellowness |
|---|---|---|
| Stearyldimethyl Benzylalkonium Chloride | 61789-81-9 | 4 |
| Alkaquat DAET-90 | 65098-88-6 | 5 |
| Stearylamidopropyl amine Hydrochloride salt | 68308-45-2 | 4 |
| Example #1 | | 2 |
| Example #10 | | 2 |
| Example #11 | | 2 |
| Example #20 | | 2 |

WET COMB OUT TEST

A laboratory test is conducted to screen the wet comb properties of a representative member of the family of novel compositions. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active product. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12-14 seconds.

| Rinse Conditioner (Wet Comb Out Test) | |
|---|---|
| Product | Time in Seconds |
| Example #1 | 11 |
| Example #20 | 13 |
| Stearyldimethylbenzyl ammonium chloride | 12 |

What is claimed is:

1. A polymeric amphoteric composition conforming to the following formula:

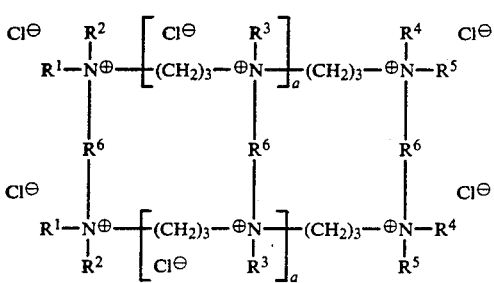

and

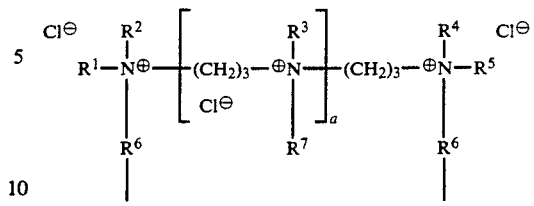

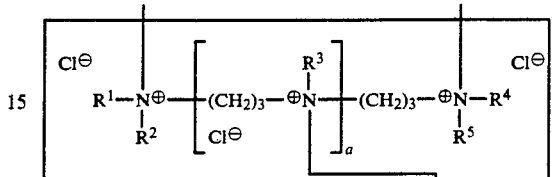

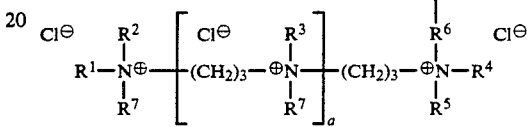

wherein;
R$^1$ is alkyl having from 6 to 40 carbon atoms;
a is an integer from 0 to 10;
b is an integer from 0 to 100;
R$^2$, R$^3$ and R$^4$ and R$^5$ are independently selected from

—CH$_2$CH$_2$COOM,

—CH(CH$_3$)CH$_2$COOM and

—CH$_2$C(CH$_3$)HCOOM;

M is a cation needed for charge balance and is selected from Na, K, NH4, Li, and Ca.

2. A composition of claim 2 wherein;
R$^1$ is selected from;

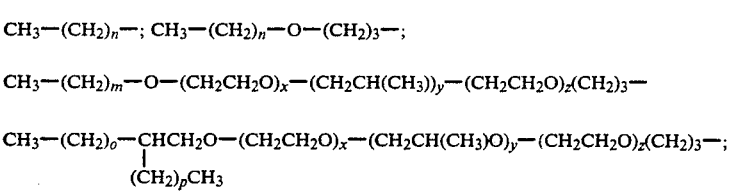

x, y, and z are independently integers from 0 to 20;
m, n, o, p are independently integers from 4 to 40;
R$^6$ is —CH$_2$CH(OH)CH$_2$—;
R$^7$ selected from H or CH$_2$CH(OH)CH$_2$OH;
M is an anion needed for charge balance and is selected from Na, K, NH4, Li, and Ca.

3. A composition of claim 1 wherein;
R$^1$ is CH$_3$—(CH$_2$)$_n$—
M is Na.

4. A composition of claim 1 wherein;
R$^1$ is CH$_3$—(CH$_2$)$_n$—O—(CH$_2$)$_3$—
M is Na.

5. A composition of claim 1 wherein R$^1$ is CH$_3$—(CH$_2$)$_m$—O—(CH$_2$CH$_2$O)$_x$—(CH$_2$CH(CH$_3$)O)$_y$—(CH$_2$CH$_2$O)$_z$(Ch$_2$)$_3$—; M is K.

6. A composition of claim 1 wherein R$^1$ is $$CH_3-(CH_2)_o-\underset{\underset{(CH_2)_pCH_3}{|}}{CH}CH_2O-(CH_2CH_2O)_x-(CH_2CH(CH_3)O)_y-(CH_2CH_2O)_z(CH_2)_3-.$$

7. A composition of claim 1 wherein n is an integer from 5 to 25.

8. A composition of claim 1 wherein n is an integer from 5 to 25.

9. A composition of claim 1 wherein x, y, and z are 0.

10. A composition of claim 1 wherein o and p are independently integers from 6 to 15.

* * * * *